United States Patent [19]
Talish et al.

[11] Patent Number: 5,730,705
[45] Date of Patent: Mar. 24, 1998

[54] ULTRASONIC TREATMENT FOR BONY INGROWTH

[76] Inventors: Roger J. Talish, 12 Knoll Rd., Fairfield, N.J. 07004-1212; John P. Ryaby, 25 Stewart Rd., Essex Fells, N.J. 07021; Michael Tanzer, 47 Aldred Crescent, Hampstead, Quebec, Canada, H3X 3H9; J. Dennis Bobyn, 53 Ballantyne North, Montreal West, Quebec, Canada, H4X 2B7

[21] Appl. No.: 661,905

[22] Filed: Jun. 12, 1996

Related U.S. Application Data

[60] Provisional application No. 60/000,161, Jun. 12, 1995.
[51] Int. Cl.[6] ............................................. A61B 17/56
[52] U.S. Cl. ............................ 601/2; 607/50; 607/7
[58] Field of Search .................... 601/2; 623/16, 623/22; 128/660.03; 607/7, 50

[56] References Cited

U.S. PATENT DOCUMENTS

| | | | |
|---|---|---|---|
| 5,201,766 | 4/1993 | Georgette | 623/16 |
| 5,556,372 | 9/1996 | Talish et al. | 601/2 |

*Primary Examiner*—Marvin M. Lateef
*Assistant Examiner*—Derrick Fields
*Attorney, Agent, or Firm*—Dilworth & Barrese

[57] ABSTRACT

Bony ingrowth adjacent a surface of a prosthetic device is provided by positioning an emitting surface of an ultrasonic applicator adjacent a skin location corresponding to an interface between bone tissue and an artificial prosthetic device located inside the body. Ultrasound is created and transmitted from the emitting surface into the body at the skin location toward at least a portion of the interface. The ultrasound is modulated to induce shear waves of acoustic energy within the bone adjacent the portion of the interface. The shear waves promote bony ingrowth at the portion of the interface.

20 Claims, 5 Drawing Sheets

ULTRASONIC TREATMENT FOR BONY INGROWTH

This application claims priority to provisional application 60/000,161, filed Jun. 12, 1995.

BACKGROUND OF THE INVENTION

1. Field of the Invention

This invention relates to the non-invasive application of ultrasound to increase and/or accelerate bone growth adjacent medical implants, such as prosthetic devices.

2. Description of the Related Art

The use of ultrasound to therapeutically treat and evaluate bone injuries is known. Impinging ultrasonic pulses having appropriate parameters, e.g., frequency, pulse repetition, and amplitude, for suitable periods of time and at a proper external location adjacent to a bone injury has been determined to accelerate the natural healing of, for example, bone breaks and fractures. For patients with reduced healing capacity, such as elderly persons with osteoporosis, ultrasonic therapy may promote healing of bone injuries that would otherwise require prosthetic replacement or leave the patient permanently disabled.

U.S. Pat. No. 4,530,360 to Duarte ("Duarte") describes a basic therapeutic technique and apparatus for applying ultrasonic pulses from an ultrasonic applicator placed on the skin at a location adjacent a bone injury. Duarte gives a range of RF signals for creating the ultrasound signal, ultrasound power density levels, a range of duration for each ultrasonic pulse, and a range of ultrasonic pulse frequencies. The length of daily treatment is also described.

The ranges described by Duarte include application of ultrasound energy with frequency in the range between 1.3 and 2 MHz in pulses of width between 10 and 2,000 microseconds and having a pulse repetition frequency between 100 and 1000 Hz. Daily treatments of 1 to 55 minutes are prescribed by Duarte, with 10 to 20 minutes being a preferred time range.

The general ranges are tailored for various specific bone injuries. For recent fractures, Duarte describes ultrasound pulses of 10 microsecond width and pulse repetition frequency of 500 Hz; a daily treatment of 10 minutes for 30 days is described as sufficient. For delayed healing, ultrasound pulses with a 50 microsecond width and pulse repetition frequency of 1000 Hz is prescribed, with the same daily treatments of 10 minutes for 30 days. For hypertrophic pseudoarthrosis, a 200 microsecond pulse width might be necessary at a 1000 Hz repetition frequency; a daily treatment of 15 minutes for 30 days might be necessary. For atrophic pseudoarthrosis, Duarte describes efficacious daily treatment as 5 minutes of 200 microsecond pulses at a 1000 Hz pulse repetition frequency, followed by 15 minutes of 2,000 microsecond pulses at a 100 Hz pulse repetition frequency, over 45 days.

Duarte also describes an ultrasound power level having a maximum intensity of 100 milliwatts per square centimeter, and a preferred power output at about this level.

U.S. Pat. No. 5,186,162 to Talish et al. ("Talish '162") describes similar ranges for the pertinent ultrasound treatment parameters. Talish '162 describes an ultrasound power level delivering an average intensity between 1 and 50 milliwatts per square centimeter to the body.

Talish '162 and U.S. Pat. No. 5,003,965 to Talish et al. ("Talish '965) describe an ultrasonic delivery system where the RF generator and transducer are both part of a modular applicator unit that is placed at the skin location. The signals controlling the duration of ultrasonic pulses and the pulse repetition frequency are generated apart from the applicator unit. Talish '965 and Talish '162 also describe fixture apparatus for attaching the applicator unit so that the operative surface is held adjacent the skin location. In Talish '965 and Talish '162, the skin is surrounded by a cast, while in U.S. Pat. No. 5,211,160 to Talish et al. ("Talish '160") fixture apparatus is described for mounting on uncovered body parts (i.e., without a cast or other medical wrapping). Talish '160 also describes various improvements to the applicator unit.

Duarte, Talish '965, Talish '162, and Talish '160, are all incorporated into this application by reference. Commonly-owned U.S. patent application Ser. Nos. 08/391,109, 08/388,971, 08/389,148 and 08/367,471 entitled Gel Containment Structure, Locator Method and Apparatus, Apparatus For Ultrasonic Bone Treatment and Acoustic System For Bone-Fracture Therapy, respectively, are also all incorporated into this application by reference.

The origins of the present invention stem from a desire to enhance bony ingrowth into, within, and around ("adjacent") internally placed prosthetic devices, such as porous coated implants. Generally, such prosthetic devices replace bone that has been damaged or degenerated, and need to "attach" to healthy bone tissue that can support the prosthetic device. Such "attachment" may be, for example, a rod (that is part of the prosthetic device) that is inserted into the medullary canal of the bone, such as that shown in FIGS. 4 and 5 and described below. The location where the bone and the prosthetic device engage will be referred to as the "interface" between the bone and the prosthetic device. Normally, once the prosthetic device is in place, the bone naturally generates and the mutual surface area of engagement (interface) between the prosthetic device and the bone increases. For example, the bone growth will fill in localized gaps at the interface, where a slight peak or valley in the surface of the bone and/or prosthetic device prevents contact. Many prosthetic devices have non-smooth surfaces that enhance the engagement between the bone and the prosthetic device as the bone grows into the contours of the surface of the prosthetic device. This natural osteogenesis of the bone adjacent the interface, known as "bony ingrowth", serves to "fasten" the bone and the prosthetic device together over time.

While the devices and methods in the above-referenced patents relate to therapeutic methods and apparatus for ultrasonically treating injured bone, they do not describe methods or systems utilizing ultrasound to promote bony ingrowth adjacent artificial prosthetic devices. It would be extremely beneficial to provide devices and methods that promote bony ingrowth in and around artificial prosthetic devices. It is likewise an object to provide such equipment and methods that are safe and simple for patient use, and which may be implemented through modest adaption of existing devices for delivering ultrasound in therapeutic settings.

SUMMARY OF THE INVENTION

The present invention includes non-invasive therapeutic apparatus and methods of increasing and accelerating bony ingrowth into and around prosthetic devices, such as porous coated implants.

In accordance with the invention, bony ingrowth adjacent a surface of a prosthetic device is stimulated and/or enhanced by positioning an emitting surface of an ultrasonic transducer adjacent a skin location corresponding to an interface between bone tissue and an artificial prosthetic device located inside the body. Ultrasound is created and transmitted from the emitting surface into the body at the skin location toward at least a portion of the interface. The ultrasound is modulated to induce shear waves of acoustic energy within the bone adjacent the portion of the interface. These shear waves aid in promoting bony ingrowth at and adjacent the interface.

In particular, an acoustic transducer is acoustically coupled to a limb or other part of a living body at an external site corresponding to the internal location of the interface between the bone and the prosthetic device. The acoustic transducer is operatively connected to a means for delivering an ultra-high-frequency carrier signal for low power excitation of the acoustic transducer. In general, an ultrasound carrier frequency between 250 KHz and 10 MHz coupled with a relatively low-frequency modulating signal (e.g., 5 Hz to 10 KHz) and low intensity acoustic signal (e.g., 5 mW/cm$^2$ to 100 mW/cm$^2$) is generated at the transducer. Surgical, non-invasive transcutaneous acoustic energy or ultrasound is delivered to body tissue and/or fluids directed toward at least a portion of a bone/implant interface. Preferable treatment times are about 20 minutes per day over a nominal period of 30 days. The acoustic energy or ultrasound delivered to the surface of the bone induces shear waves within the bone adjacent the interface, enhancing the bony ingrowth.

BRIEF DESCRIPTION OF THE DRAWINGS

Preferred embodiments of the invention are described below with reference to the drawings, which are described as follows.

DETAILED DESCRIPTION OF THE PREFERRED EMBODIMENTS

The ultrasonic treatment apparatus of the present invention is used for therapeutically promoting bony ingrowth adjacent prosthetic devices using ultrasound. The apparatus preferably includes an ergonomically constructed ultrasonic transducer assembly partially fabricated with a conductive plastic material. The apparatus also utilizes a portable, ergonomically constructed main operating unit (MOU) which provides control signals for the ultrasonic transducer treatment head module. The portable MOU may be constructed to fit within a pouch worn by the patient.

Figure 1:
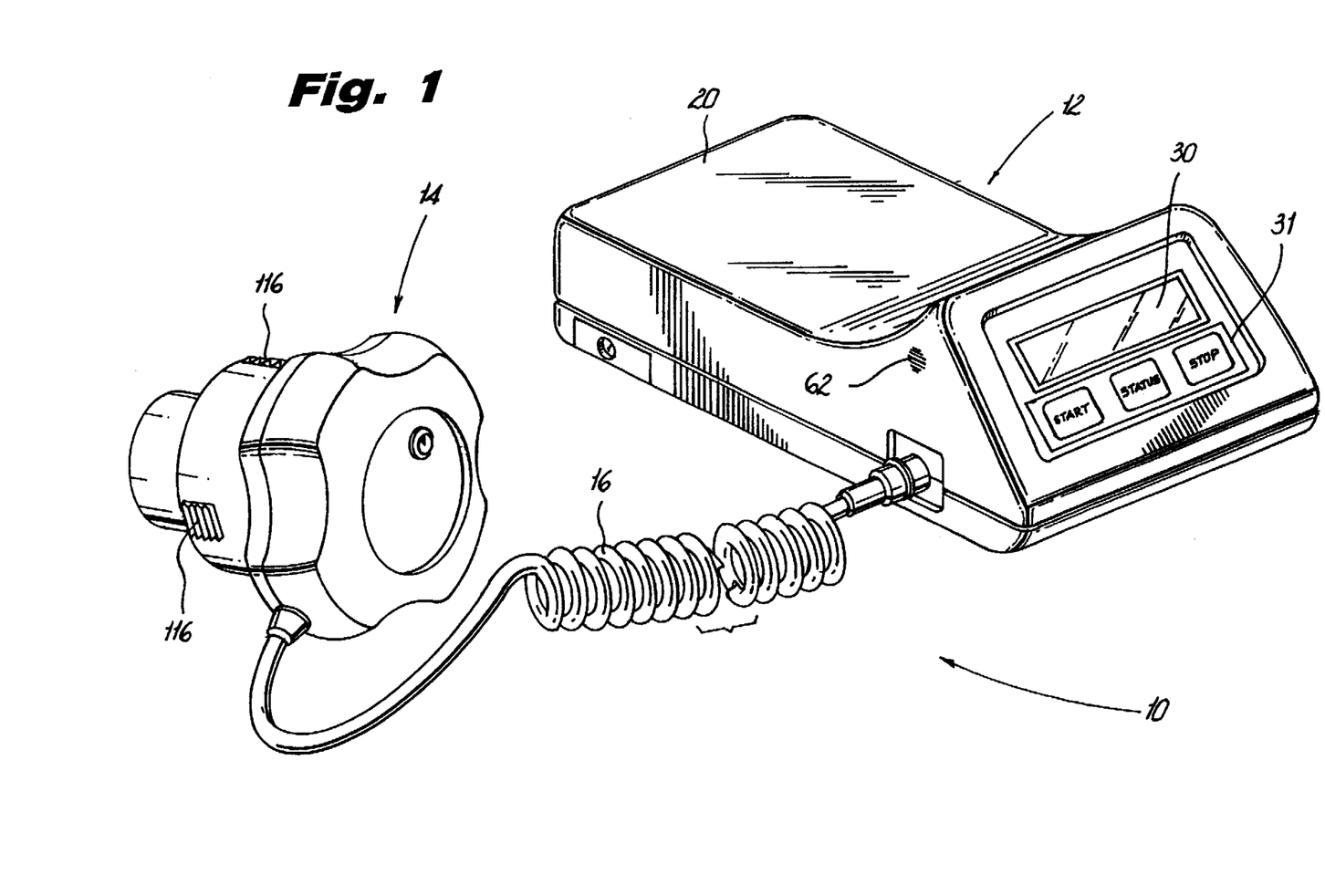
FIG. 1 is a perspective view of a portable ultrasonic treatment apparatus according to the present invention, illustrating a main operating unit or controller and an ultrasonic transducer treatment head module.
Figure 2:
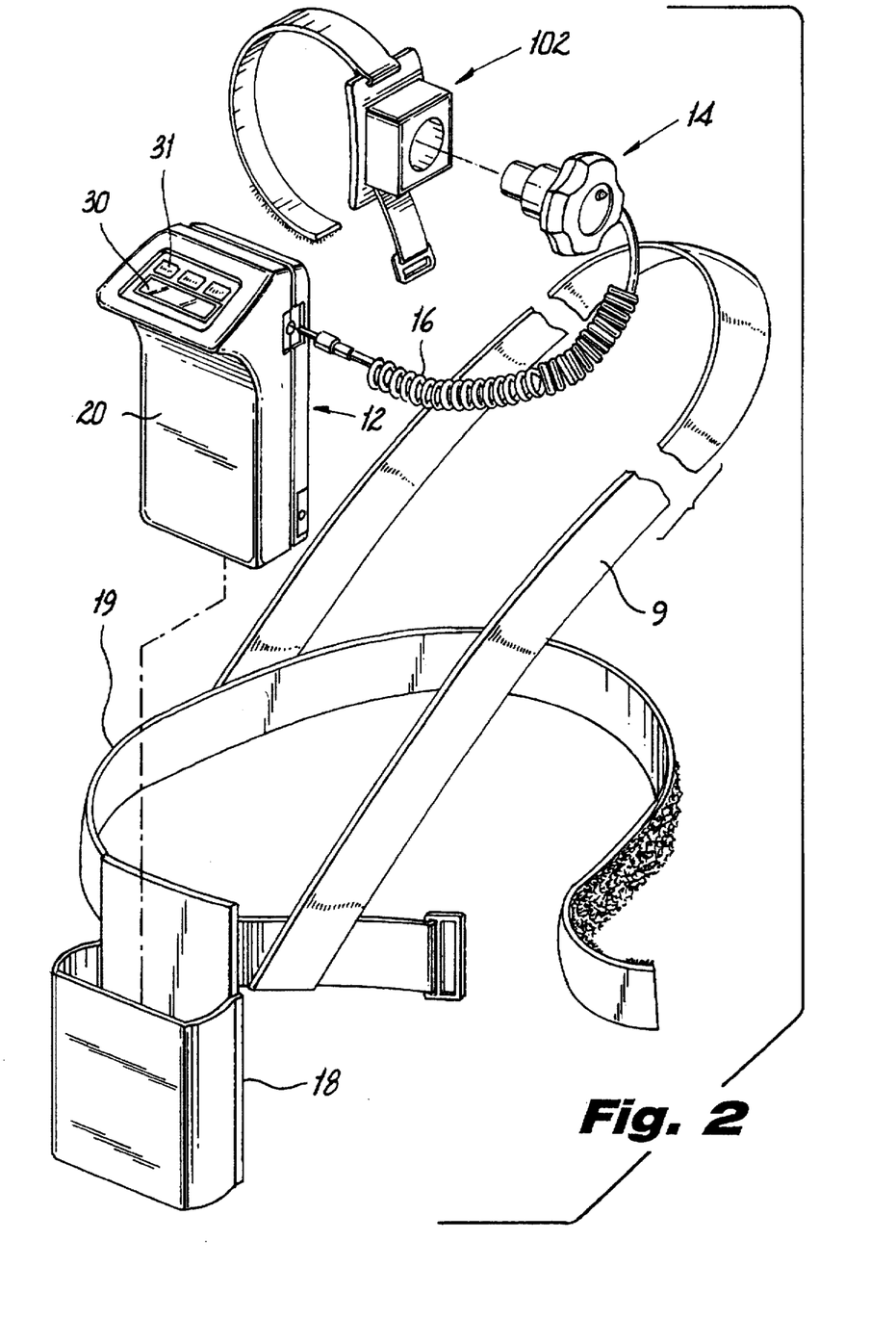
FIG. 2 is a perspective view with parts separated of the main operating unit and transducer head module of FIG. 1 and a pouch shoulder strap and belt for patient mobility during treatment.
Figure 3:
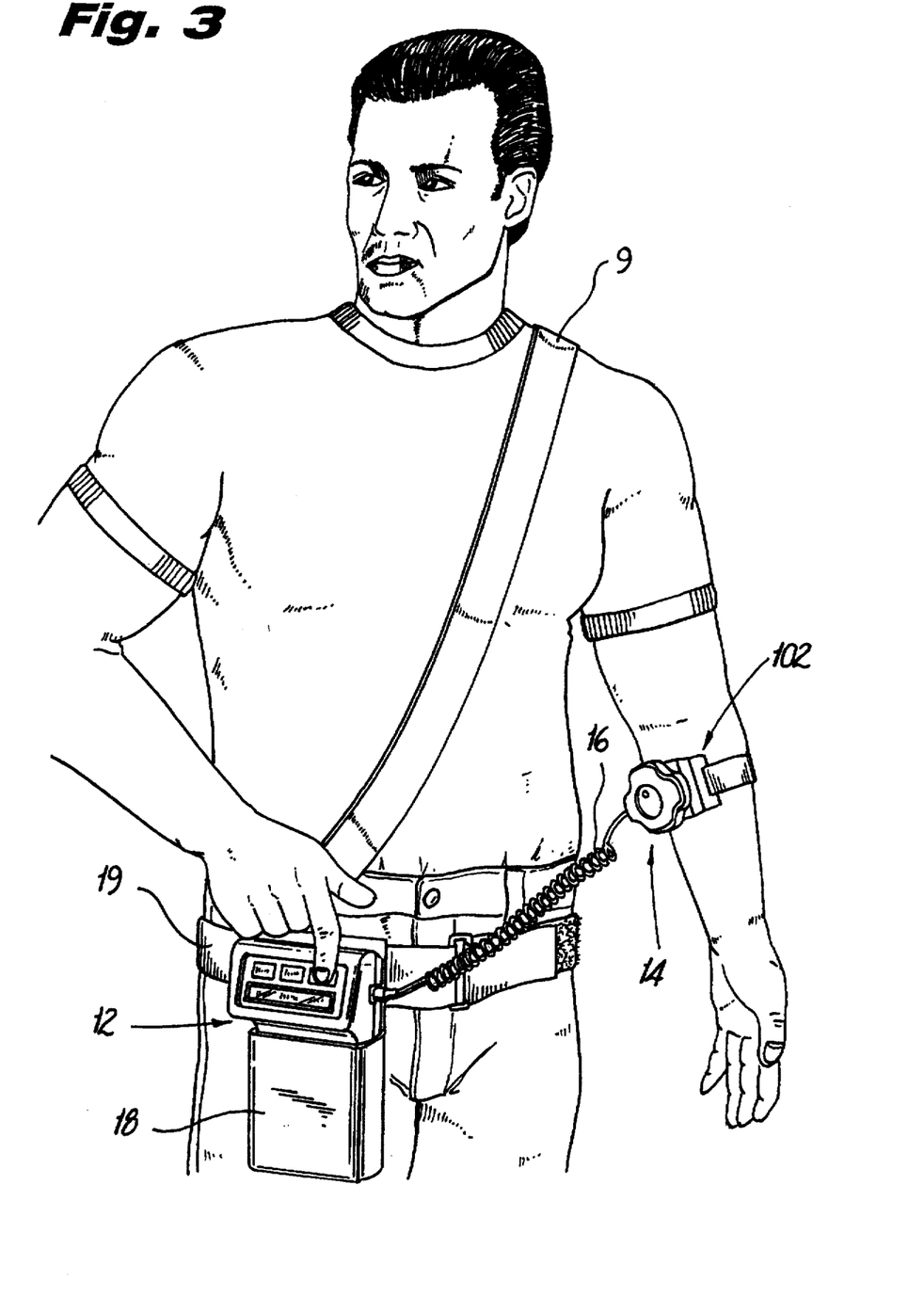
FIG. 3 is a perspective view of a patient wearing the portable treatment apparatus according to the present invention during treatment.

Turning to the figures, in particular FIG. 1, the portable ultrasonic treatment apparatus 10 of the present invention is shown. The ultrasonic treatment apparatus 10 includes an MOU 12 and an ultrasonic transducer treatment head module 14 coupled to the MOU 12 by cable 16. The MOU 12 is ergonomically configured and constructed to fit with a pouch 18 which may be worn by the patient using belt 19 and shoulder strap 9, for example, as shown in FIGS. 2 and 3. Cable 16 is preferably a multi-conductor cable capable of transmitting relatively low frequency or optical signals, as well as digital signals. Cable 16 may include coaxial cable or other type of suitable conductor. Alternatively, cable 16 may include fiber optic cable for transmitting optical signals. Attachment 102 is used to fasten the treatment head module 14 with the transducer surface adjacent the skin.

The electronics for the MOU 12 described in commonly-owned U.S. patent application Ser. No. 08/389,148, incorporated by reference above, allows the physician to set the RF signals for creating the carrier frequency of the ultrasound, the ultrasound power density levels and the modulating frequency of the ultrasound. (Where the ultrasound is carried on pulses rather than modulated continuously at a low frequency, the range of duration for each ultrasonic pulse and the ultrasonic pulse frequencies may be set.) The treatment time may also be pre-set by the physician, so that the patient may simply position the transducer treatment head module 14 adjacent the skin location, and turn the device on. Appropriate control signals are transmitted from the MOU 12 to the transducer treatment head module 14 so that the transducer surface is driven at the frequency and power levels to create the desired ultrasound. Ultrasound is delivered by the device to the skin location at the requisite levels for the predetermined period of time.

Figure 4:
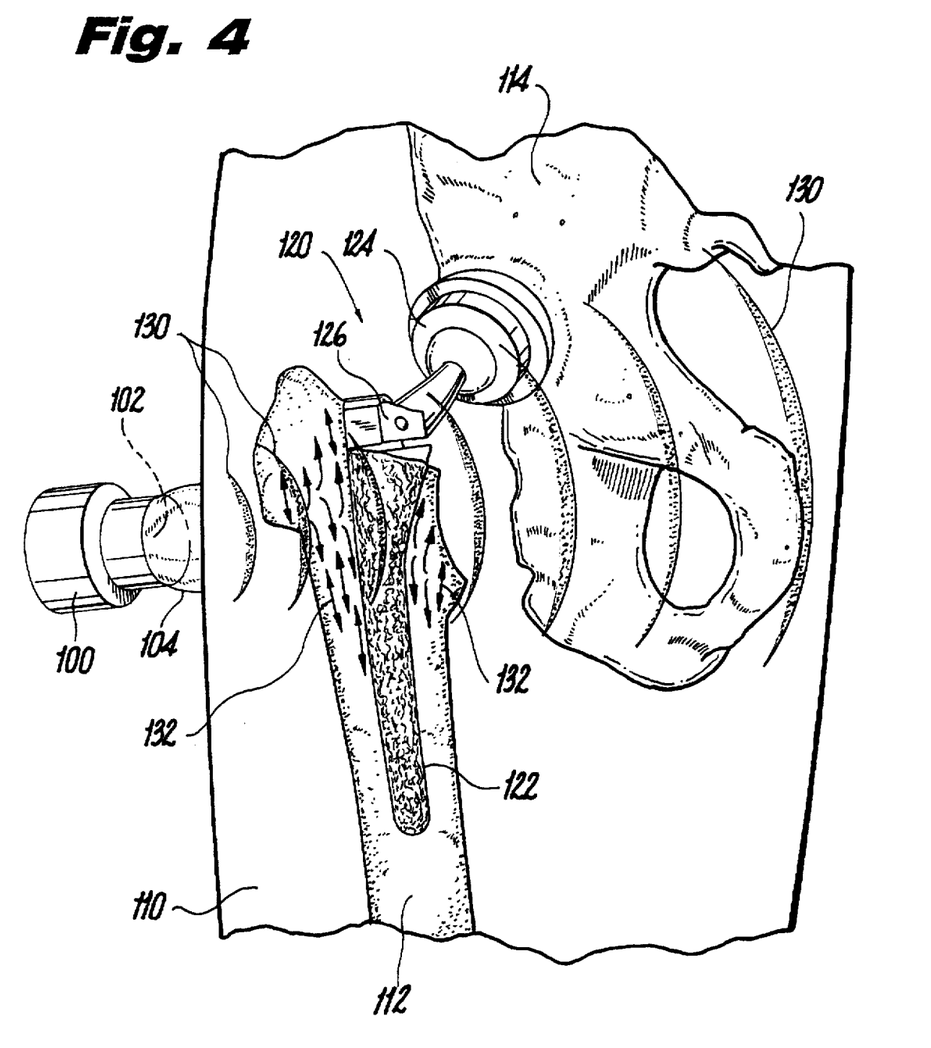
FIG. 4 is a perspective view of an ultrasonic treatment head module positioned adjacent a skin location and transmitting therapeutic ultrasound treatment to the interface between a bone and an artificial prosthetic device within the body.

FIG. 4 illustrates delivery of ultrasonic therapy to a prosthetic replacement of the hip in accordance with the present invention. A transducer treatment head module 100, such as that shown in FIGS. 1–3 above, is placed at a skin location corresponding to the region of the prosthetic device 120.

Figure 5:
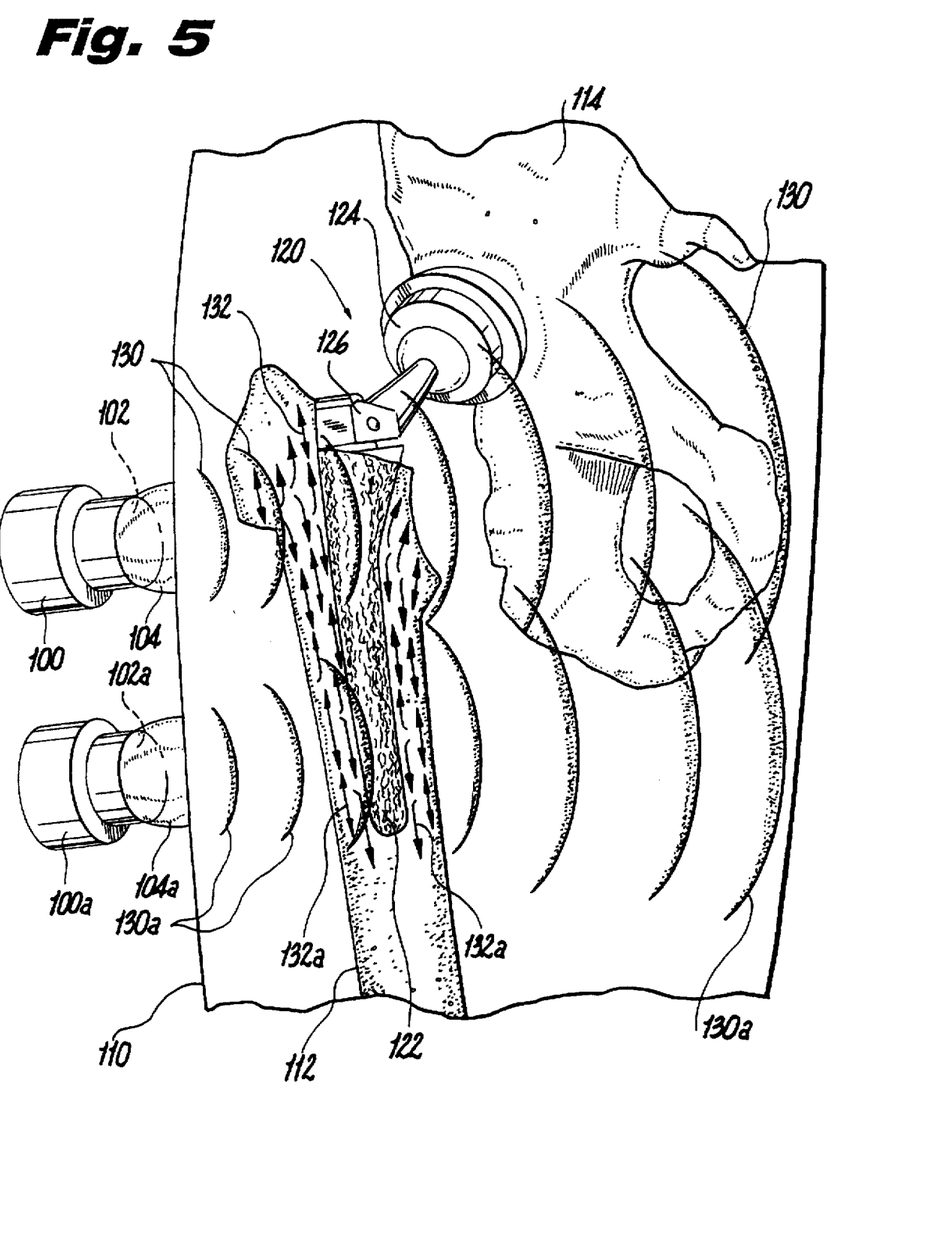
FIG. 5 is a perspective view of two ultrasonic treatment head modules positioned adjacent skin locations and transmitting therapeutic ultrasound treatment to the interface between a bone and an artificial prosthetic device within the body.

(To facilitate the description, only the treatment head module 100 of the ultrasonic device is shown in FIG. 4 (and FIG. 5). It will be understood that the treatment head module 100 is linked by a cable to an MOU, as shown in FIGS. 1–3, above, and further described in U.S. patent application Ser. No. 08/389,148. Also not shown in FIG. 4 (and FIG. 5) is an attachment that interfaces with the body that holds the transducer surface 102 of the treatment head module 100 adjacent the skin location. Such attachment apparatus is shown in FIGS. 2 and 3 and described in commonly-owned U.S. patent application Ser. No. 08/388,971, incorporated by reference above. As shown, conductive gel and/or a gel containment structure 104 is usually interposed between the transducer surface 102 and the skin in order to increase the efficiency of transmission of the ultrasound from the transducer surface 102 into the soft tissue 110 of the body.

In FIG. 4, a prosthetic device 120 is shown replacing the natural body joint between the head of the right femur 112 and the Acetabulum of the pelvis 114. The head of the right femur 112 is shown removed for one of a number of medical reasons, such as degeneration of the bone or a trauma without the possibility of healing or regeneration. A socket portion 124 attaches the prosthetic device 120 to the hip 114 at the Acetabulum, and a rod portion 122 inserted into the medullary canal of the femur 112 attaches the prosthetic device 120 to the femur 112. A multi-directional joint 126 connecting the socket portion 124 and the rod portion 122 provides a range of movement of the femur 112 with respect to the pelvis 114.

Rod portion 122 has a rough surface that serves to "attract" bony ingrowth of the femur 112 adjacent the interface between the rod portion 122 and the femur 112. Bony ingrowth adjacent such a rough surface implies a more rigorous connection between the femur 112 and the rod portion 122 will develop, as the bony ingrowth "fills in" the local high and low points of the interface between the rod portion 122 and femur 112.

Treatment head module 100 delivers an ultrasonic wave 130 through the gel containment structure 102 and into the soft tissue 110 surrounding the femur 112. The ultrasonic wave travelling through the soft tissue 110 has a primary component in the longitudinal direction (represented by wave fronts having reference numbers 130 shown radiating outward from the transducer surface 102). The ultrasonic wave 130 diverges as it travels through the soft tissue medium, so that the ultrasonic wave 130 is incident on a relatively large cross-section of the femur 112. The longitudinal wave fronts 130 incident on the surface of the femur 112 are absorbed. If there is no fracture in the femur 112, a surface acoustic wave is induced at the surface and within the femur 112. The surface acoustic wave, or shear wave, is represented by wave fronts having reference numbers 132.

The surface acoustic wave 132 delivers therapeutic treatment to the femur 112 by inducing currents and the like within the bone tissue material to be a piezolelectric This treatment promotes osteogenesis and enhances bony ingrowth adjacent the rod portion 122 of the prosthetic device 120.

As noted above, the carrier frequency of the ultrasonic wave generated at the transducer 102 may be between 250 kHz and 10 MHz and may be modulated by a relatively low-frequency signal (e.g., 5 Hz to 10 kHz). The power density at the transducer surface 102 is between 5 mW/cm$^2$ and 100 mW/cm$^2$. The preferable time of treatment is about 20 minutes per day over a period of days. These ranges and nominal treatment values are adjusted based on the particular circumstances: The carrier frequency and the power density is adjusted according to the amount of soft tissue 110 (including the density of the soft tissue 110) that must be penetrated by the ultrasonic wave, and the amplitude of the shear wave desired within the bone. Accordingly, treatment for the prosthetic device 120 as in FIG. 4, where there is a large interface between the femur 112 and the rod portion 122, with a relatively large amount of soft tissue interposed between the interface and the skin location, may require treatment at the upper limits of the ranges for the carrier frequency and the power density. Where the interface is relatively small, and there is less soft tissue to be penetrated, settings toward the lower limits are sufficient. Similarly, the number of days of treatment will depend on the characteristics and location of the interface.

As shown in FIG. 5, more than one transducer treatment head module may be used to stimulate larger areas, as needed. In FIG. 5, a second transducer treatment head module 100a is shown positioned at a skin location below the module 100 of FIG. 4. The ultrasonic waves 130, 130a emitted by each respective treatment head module 100, 100a diverge and overlap as they travel through the soft tissue 110, so that the ultrasound is incident on a large cross-section of the femur 112.

The ultrasound incident on the femur 112 is converted into shear waves 132, 132a which, because of the larger cross-section of the femur 112 covered by the ultrasound, are adjacent to the entire interface between the femur 112 and the rod portion 122. Thus, the shear waves 132, 132a will promote bony ingrowth along the entire interface. (The shear waves 130 at the portion of the femur 112 adjacent the upper half of the rod portion 122 are primarily induced by the absorption of the longitudinal wave 130 created by the upper treatment head module 100, while the shear waves 130a at the portion of the femur 112 adjacent the lower half of the rod portion 122 are primarily induced by the absorption of the longitudinal waves 130a created by the lower treatment head module 100a. However, this distinction is made to facilitate the description only. In reality, there is overlap between the shear waves created by the two treatment head modules: The upper treatment head module 100 will create shear waves (albeit attenuated) adjacent the lower half of the rod portion 122, and the lower treatment head module 100a will create shear waves (albeit attenuated) adjacent the upper half of the rod portion 122.)

Also, while FIG. 5 illustrates the treatment head modules 100, 100a creating ultrasound 130, 130a (and the resulting shear waves 132, 132a) at the same time, this may not be essential, or even preferable, for certain bony ingrowth therapy. Where the transmissions from multiple treatment heads are simultaneous, there will be interference between ultrasound signals, resulting in local maxima and minima of intensity of the longitudinal wave incident at the bone surface. Consequently, shear waves of varying intensity within the bone and along the interface will be induced. Slowly sweeping the low frequency signal of emission for one or more modules will shift the interference pattern of the longitudinal wave at the bone surface, and the shear wave intensity gradient within the bone. This may be a desirable method of treatment for focusing and promoting various types of bony ingrowth at certain regions of the interface.

On the other hand, if shear waves of a more uniform intensity are desired at the interface, it may be preferable to transmit the ultrasound from the various treatment head modules in sequence, to lessen or eliminate the interference of the longitudinal waves and the shear waves induced within the bone.

The ultrasonic applicators (the transducer treatment head modules 100, 100a in FIGS. 4 and 5) may be moved (or configured so that they are movable) to different skin locations in order to provide the shear waves that promote bony ingrowth to various portions of the interface between the prosthetic device 120 and the femur 112. Varying the position, including moving the transducer surfaces 102, 102a circularly or linearly along the skin locations, also provides shear waves of varying intensities at the interface. Such movement, in effect, will provide a more uniform intensity shear wave over time at a broader region of the interface, thereby promoting more uniform bony ingrowth at a larger region of the interface.

In general, the transducer module(s) may also be configured so that it vibrates with respect to the skin location, so that the longitudinal wave transmitted through the soft tissue is more uniform, thus providing more uniform treatment (including more uniform shear waves) at the portion of the bone the longitudinal wave impinges. The transducer module may be made to vibrate with respect to an attachment which holds it adjacent the skin location (omitted from FIGS. 4 and 5 for clarity, but shown, for example, in FIG. 3) to accomplish this. As noted above, such movement will, in effect, provide a more uniform intensity shear wave over time at a broader region of the interface, thereby promoting more uniform bony ingrowth at a larger region of the interface.

Similarly, the transducer surface may be made of segments of various shapes, in order to allow differing patterns and intensities of ultrasonic waves to be transmitted toward the interface. This provides a variety of therapeutic ultrasonic stimulation and treatment at the interface. The segments may be pie shaped, annular rings, or other configurations, and they may be activated separately or together. Alternatively, or in conjunction, the transducer may be provided with a modal converter or transducer lens, which may also change the pattern of the ultrasound emitted from the transducer.

The carrier frequency and/or the modulating frequency may also be varied or "swept" through a range of frequencies in order to provide a variety of treatment to the interface. The frequencies may be varied either in a continuous manner, or discrete changes may be made.

Not only will varying the patterns, intensity, the carrier frequency and/or modulating frequency promote more uniform bony ingrowth over a larger portion of the interface, it is also useful in applying ultrasonic treatment to promote a variety of different bony ingrowth in approximately the same region during the same therapy session. Where the prosthetic device has a "rough" surface, for example, it may be necessary to enhance bony ingrowth at the interface toward the surface of the prosthetic device, as well as along the surface. Such variations in the ultrasound will promote diverse bony ingrowth at the interface.

Also, varying the patterns, intensity, the carrier frequency and/or modulating frequency is useful in applying ultrasonic treatment to promote bony ingrowth at different portions of the interface that may be at different depths within the bone and/or soft tissue.

It will be understood that various modifications can be made to the various embodiments of the present invention herein disclosed without departing from its spirit and scope. For example, various sizes and shapes of the ultrasonic treatment applicator are contemplated for delivering ultrasonic waves of various intensities and/or profiles to the interface between the bone and the prosthetic device. Also, various modifications may be made in the method of treatment. For example, ultrasonic treatment applicators may be positioned at skin locations surrounding the prosthetic device, if necessary. Similarly, various modifications may be made to the above-described sequence of the invention in method without departing from its spirit and scope. For example, a single ultrasonic treatment applicator may be positioned along one portion of the interface to promote rapid bony ingrowth where it is most important to strengthen the structural connection between the prosthetic device and the bone. Later, a multiplicity of ultrasonic treatment applicators emitting at a lower intensity may be used to strengthen the overall connection at the interface. Promotion of bony ingrowth at interfaces between any bone and prosthetic device is also contemplated. Therefore the above description should not be construed as limiting the invention but merely as presenting preferred embodiments of the invention. Those skilled in the art will envision other modifications within the scope and spirit of the present invention as defined by the claims presented below.

What is claimed is:

1. A method for promoting bony ingrowth adjacent a surface of a prosthetic device comprising the steps of:

a. positioning an emitting surface of an ultrasonic applicator at a skin location corresponding to an interface between bone tissue and a prosthetic device located inside a body;

b. transmitting ultrasound from the emitting surface into the body at the skin location, the ultrasound directed toward at least a portion of the interface; and c. modulating the ultrasound emitted at the emitting surface to induce shear waves of acoustic energy within the bone adjacent the portion of the interface.

2. A method as in claim 1, wherein the step of positioning an emitting surface of an ultrasonic applicator adjacent a skin location includes positioning an ultrasonic treatment head module with its emitting surface adjacent the skin location.

3. A method as in claim 2, wherein the step of positioning the ultrasonic treatment head module with its emitting surface adjacent the skin location includes engaging the ultrasonic treatment head module adjacent the skin location by using an attachment.

4. A method as in claim 2, wherein the step of transmitting ultrasound from the emitting surface into the body at the skin location includes the step of providing control signals to the ultrasonic treatment head module from a main operating unit.

5. A method as in claim 1, wherein the step of transmitting ultrasound from the emitting surface into the body at the skin location includes the step of providing signals to the emitting surface to drive the surface.

6. A method as in claim 1, wherein the step of transmitting the ultrasound includes directing it at a prosthetic device connecting a pelvis and a femur.

7. A method as in claim 1, wherein the step of modulating the ultrasound includes the step of creating ultrasound having a carrier frequency in a range of about 250 kHz to about 10 MHz.

8. A method as in claim 1 wherein the step of modulating the ultrasound includes the step of creating ultrasound with a carrier frequency modulated by low-frequency signal in the range of about 5 Hz to about 10 kHz.

9. A method as in claim 1, wherein the step of modulating the ultrasound includes the step of transmitting the ultrasound from the emitting surface into the body at the skin location with a power density in a range between about 5 mW/cm$^2$ and 100 mW/cm$^2$.

10. A method as in claim 1, wherein the step of modulating the ultrasound includes the step of transmitting the ultrasound from the emitting surface into the body at the skin location for a treatment period of about twenty minutes.

11. A method as in claim 1, wherein the step of modulating the ultrasound emitted to induce shear waves of acoustic energy within the bone includes adjusting the carrier frequency as a function of dimensions of the interface.

12. A method as in claim 1, wherein the step of modulating the ultrasound emitted to induce shear waves of acoustic energy within the bone includes adjusting the power density at the emitting surface as a function of characteristics of the interface.

13. A method as in claim 1, wherein the step of modulating the ultrasound emitted to induce shear waves of acoustic energy within the bone includes adjusting the carrier frequency as a function of the amount of tissue interposed between the skin location and the bone.

14. A method as in claim 1, wherein the step of modulating the ultrasound emitted to induce shear waves of acoustic energy within the bone includes adjusting the power density at the emitting surface as a function of the amount of tissue interposed between the skin location and the bone.

15. A method as in claim 1, wherein the step of modulating the ultrasound emitted to induce shear waves of acoustic energy within the bone includes varying the frequency of the carrier wave emitted over time.

16. A method as in claim 1, wherein the step of modulating the ultrasound emitted to induce shear waves of acoustic energy within the bone includes varying the position of the emitting surface of the ultrasonic applicator adjacent the skin location.

17. A method for promoting bony ingrowth adjacent a surface of a prosthetic device comprising the steps of:
   a. positioning emitting surfaces of two or more ultrasonic applicators at skin locations corresponding to an interface between bone tissue and a prosthetic device located inside a body;
   b. transmitting ultrasound from each emitting surface into the body at the respective skin location, the ultrasound directed toward at least a portion of the interface; and
   c. modulating tile ultrasound emitted by each emitting surface to induce shear waves of acoustic energy within the bone adjacent the respective portion of the interface.

18. A method as in claim 17, wherein the step of positioning emitting surfaces of two or more ultrasonic applicators at skin locations adjacent to an interface between bone tissue and an artificial prosthetic device located inside the body includes positioning the emitting surfaces to be directed at different regions of the interface.

19. A method as in claim 18, wherein the step of positioning the emitting surfaces so they are directed at different regions of the interface induces shear waves of acoustic energy within the bone adjacent substantially all of the interface.

20. A method as in claim 17, wherein the step of modulating the ultrasound emitted by each emitting surface includes transmitting the ultrasound from the two or more emitting surfaces sequentially.

* * * * *